(12) United States Patent
Reinecke et al.

(10) Patent No.: US 7,276,038 B2
(45) Date of Patent: Oct. 2, 2007

(54) FIELD ADJUSTABLE TRACTION DEVICE

(75) Inventors: Steven M. Reinecke, Dallas, TX (US); Paul J. Vasta, Jr., McKinney, TX (US)

(73) Assignee: Amei Technologies Inc., Wilmington, DE (US)

( * ) Notice: Subject to any disclaimer, the term of this patent is extended or adjusted under 35 U.S.C. 154(b) by 553 days.

(21) Appl. No.: 10/393,541

(22) Filed: Mar. 20, 2003

(65) Prior Publication Data

US 2004/0138599 A1 Jul. 15, 2004

Related U.S. Application Data

(60) Provisional application No. 60/440,070, filed on Jan. 14, 2003.

(51) Int. Cl.
*A61F 5/00* (2006.01)

(52) U.S. Cl. .......................... 602/19; 602/32

(58) Field of Classification Search ................ 602/32, 602/36, 19, 5, 38, 60–61; 2/311, 338; 606/237, 606/240, 241, 242; 128/876, 96.1, 99.1, 128/100.1, 845, 872–875, 95.1, 869
See application file for complete search history.

(56) References Cited

U.S. PATENT DOCUMENTS

| | | | | |
|---|---|---|---|---|
| 1,589,670 A | * | 6/1926 | Vartia | 602/36 |
| 2,453,370 A | * | 11/1948 | Hittenberger | 602/19 |
| 2,554,337 A | * | 5/1951 | Lampert | 606/237 |
| 2,835,247 A | * | 5/1958 | Stabholc | 602/19 |
| 3,029,810 A | | 4/1962 | Martin | |
| 3,052,236 A | * | 9/1962 | Schrieber | 602/13 |
| 3,351,053 A | * | 11/1967 | Stuttle | 602/19 |
| 3,420,230 A | | 1/1969 | Ballard | |
| 3,521,623 A | | 7/1970 | Nichols et al. | |
| 3,548,817 A | * | 12/1970 | Mittasch | 602/36 |
| 3,598,114 A | | 8/1971 | Lewis | |
| 3,889,664 A | * | 6/1975 | Heuser et al. | 602/36 |
| 3,926,182 A | | 12/1975 | Stabholz | |
| 4,135,503 A | | 1/1979 | Romano | |
| 4,178,922 A | | 12/1979 | Curlee | |
| 4,269,179 A | | 5/1981 | Burton et al. | |
| 4,497,517 A | | 2/1985 | Gmeiner et al. | |
| 4,545,370 A | * | 10/1985 | Welsh | 602/19 |
| 4,552,135 A | | 11/1985 | Racz et al. | |
| 4,559,933 A | | 12/1985 | Batard et al. | |
| 4,599,998 A | | 7/1986 | Castillo | |
| 4,622,957 A | | 11/1986 | Curlee | |
| 4,682,587 A | | 7/1987 | Curlee | |
| 4,682,588 A | | 7/1987 | Curlee | |
| 4,685,668 A | | 8/1987 | Newlin, Jr. | |

(Continued)

*Primary Examiner*—Patricia Bianco
*Assistant Examiner*—Huong Q. Pham
(74) *Attorney, Agent, or Firm*—Baker & McKenzie LLP (57) ABSTRACT

In one embodiment, a fastening mechanism is provided for a field adjustable traction device having first and second supports coupled using one or more lifting mechanisms. A set of one or more posts are configured to be inserted through a set of one or more holes formed in a back strap of a support and also through a selected one of a number of sets of one or more holes formed in a front strap of the support to position the front strap relative to the back strap. A mechanism is configured to engage the set of one or more posts to secure the front strap in position relative to the back strap.

12 Claims, 5 Drawing Sheets

U.S. PATENT DOCUMENTS

| | | |
|---|---|---|
| 4,691,696 A | 9/1987 | Farfan de los Godos |
| 4,702,235 A | 10/1987 | Hong |
| 4,715,362 A | 12/1987 | Scott |
| 4,721,102 A * | 1/1988 | Pethybridge ............... 602/19 |
| 4,802,667 A * | 2/1989 | Altner ..................... 482/93 |
| 4,836,194 A | 6/1989 | Sebastian et al. |
| 4,884,562 A | 12/1989 | Stone |
| 4,898,185 A | 2/1990 | Fuller |
| 4,907,575 A | 3/1990 | Satterthwaite |
| 4,991,572 A | 2/1991 | Chases |
| 4,991,573 A | 2/1991 | Miller |
| 5,060,640 A | 10/1991 | Rasmusson |
| 5,062,414 A | 11/1991 | Grim |
| 5,105,803 A * | 4/1992 | Burton ..................... 602/36 |
| 5,111,807 A | 5/1992 | Spahn et al. |
| 5,144,943 A | 9/1992 | Luttrell et al. |
| 5,188,586 A | 2/1993 | Castel et al. |
| 5,195,948 A | 3/1993 | Hill et al. |
| 5,207,635 A | 5/1993 | Richards et al. |
| 5,256,135 A | 10/1993 | Avihod |
| 5,363,863 A * | 11/1994 | Lelli et al. ............... 128/876 |
| 5,382,226 A | 1/1995 | Graham |
| RE34,883 E | 3/1995 | Grim |
| 5,403,266 A | 4/1995 | Bragg et al. |
| 5,437,615 A | 8/1995 | Pekar et al. |
| 5,437,617 A | 8/1995 | Heinz et al. |
| 5,441,479 A | 8/1995 | Chitwood |
| 5,450,858 A | 9/1995 | Zablotsky et al. |
| 5,462,518 A | 10/1995 | Hatley et al. |
| D366,555 S * | 1/1996 | Daniels ..................... D2/627 |
| 5,586,969 A | 12/1996 | Yewer, Jr. |
| 5,647,824 A * | 7/1997 | Levenson .................. 482/92 |
| 5,651,764 A | 7/1997 | Chiu |
| 5,681,267 A | 10/1997 | Molino et al. |
| 5,690,609 A | 11/1997 | Heinze, III |
| 5,695,452 A | 12/1997 | Grim et al. |
| 5,722,940 A | 3/1998 | Gaylord, Jr. et al. |
| 5,724,993 A | 3/1998 | Dunfee |
| 5,853,378 A * | 12/1998 | Modglin ................... 602/19 |
| 5,911,697 A * | 6/1999 | Biedermann et al. ........ 602/19 |
| 5,913,410 A | 6/1999 | Tsuchiya |
| 5,916,188 A | 6/1999 | Ousdal |
| 5,950,628 A * | 9/1999 | Dunfee ..................... 128/874 |
| 6,099,490 A | 8/2000 | Turtzo |
| 6,146,345 A | 11/2000 | Mignard |
| 6,331,170 B1 | 12/2001 | Ordway |
| 6,364,186 B1 | 4/2002 | Gilmour et al. |
| 6,500,137 B1 * | 12/2002 | Molino et al. ............. 602/19 |
| 6,533,740 B2 | 3/2003 | Reinecke et al. |
| 6,635,025 B1 | 10/2003 | Reinecke et al. |
| 6,689,082 B2 * | 2/2004 | Reinecke et al. ........... 602/32 |
| 6,702,771 B1 | 3/2004 | Reinecke et al. |
| 6,964,644 B1 * | 11/2005 | Garth ....................... 602/19 |
| 2003/0097085 A1 | 5/2003 | Reinecke et al. |
| 2003/0195446 A1 | 10/2003 | Reinecke et al. |
| 2003/0208147 A1 | 11/2003 | Reinecke et al. |

\* cited by examiner

FIELD ADJUSTABLE TRACTION DEVICE

RELATED APPLICATION

This application claims the benefit under 35 U.S.C. § 119(e) of U.S. Provisional Application Ser. No. 60/440,070 filed Jan. 14, 2003 entitled "Field Adjustable Traction Device."

TECHNICAL FIELD OF THE INVENTION

This invention relates to the field of medical devices, and more particularly to a field adjustable traction device.

BACKGROUND OF THE INVENTION

People have long dealt with the pain, aggravation and loss of productivity arising from spinal injuries, particularly those to the low back. Most people will at some point in their lives be at least temporarily incapacitated by low back pain. The relative ease with which injuries to the spine and supporting musculature are incurred, as well as the debilitating effects of even slight injuries, merely adds to the overall severity of the problem of dealing with spinal injuries. The forms of treatment vary over the length of time that the patient experiences pain. Eighty percent of low back pain sufferers will heal over six weeks with minimal intervention. However, the remaining twenty percent of sufferers create the greatest challenges and cost to the medical system. After the acute phase, surgical intervention or more invasive forms of treatment may be selected, but minimally-invasive or non-invasive treatments are preferred where appropriate. Another concern when dealing with spinal injuries is rehabilitation. Because spinal injuries do not typically heal within a matter of days, effective rehabilitation techniques are often very important for successful healing and recovery.

SUMMARY OF THE INVENTION

In one embodiment, a field adjustable traction device includes a first support belt, a second support belt separated from the first support belt such that a user's joint may be positioned between the support belts, and one or more lifting mechanisms coupling the support belts and operable to apply a decompressive force to the joint through the support belts. Each support belt includes a back strap having first and second ends, a set of one or more holes being formed in the back strap proximate the first end and a set of one or more holes being formed in the back strap proximate the second end. Each support belt also includes first and second front straps adjustably fastened to the first and second ends of the back strap, respectively. A number of sets of one or more holes are formed in the first front strap, each set of one or more holes formed in the first front strap being configured to align with the set of one or more holes proximate the first end of the back strap. A number of sets of one or more holes are also formed in the second front strap, each set of one or more holes formed in the second front strap being configured to selectively align with the set of one or more holes proximate the second end of the back strap. For each front strap, a set of one or more posts may be inserted through the set of one or more holes formed in the back strap proximate a corresponding end of the back strap and also through a selected one of the sets of one or more holes formed in the front strap to position the front strap relative to the back strap. For each front strap, a mechanism may engage the set of one or more posts to secure the front strap in position relative to the back strap.

In another embodiment, a fastening mechanism is provided for use in a field adjustable traction device having a first support belt, a second support belt separated from the first support belt such that a user's joint may be positioned between the support belts, and one or more lifting mechanisms coupling the support belts and operable to apply a decompressive force to the joint through the support belts. Each of the support belts includes a back strap and two front straps each coupled to a corresponding end of the back strap. The fastening mechanism includes a fastener insert having a base and a set of one or more posts extending from the base. The set of one or more posts are configured to be inserted through a set of one or more holes formed in a back strap of a support proximate an end of the back strap and also through a selected one of a number of sets of one or more holes formed in a front strap of the support to position the front strap relative to the back strap. The fastening mechanism also includes fastener ring having a body and a set of one or more channels formed in the body. The set of one or more posts of the fastener insert are operable to engage with the set of one or more channels to secure the front strap in position relative to the back strap when the fastener ring is positioned so as to surround the back strap, front strap, and fastener insert proximate the selected set of one or more holes formed in the front strap.

In another embodiment, a method is provided for fitting a field adjustable traction device to a user, where the traction device has a first support belt, a second support belt separated from the first support belt such that a joint of the user may be positioned between the support belts, and one or more lifting mechanisms coupling the support belts and operable to apply a decompressive force to the joint through the support belts, and where each support belt includes a back strap and two front straps each coupled to a corresponding end of the back strap. The method includes aligning a selected one of a number of sets of one or more holes formed in a front strap of a support with a set of one or more holes formed in a back strap of the support proximate an end of the back strap. The method also includes inserting a set of one or more posts through the set of one or more holes formed in the back strap and also through the selected set of one or more holes formed in the front strap to position the front strap relative to the back strap. The method further includes engaging the set of one or more posts to secure the front strap in position relative to the back strap.

Particular embodiments of the present invention provide one or more technical advantages. For example, certain embodiments provide a traction device that may be worn by a user to reduce the compressive forces on the user's spine by transferring at least a portion of the user's upper body weight off of the spine to the user's hips. In particular, the decompressive forces generated by the device may be concentrated on the lower spine of the user, an area that may be commonly injured due to compressive forces. The traction device may also provide stabilization of the torso to prevent additional compressive forces in the spine due to bending and lifting by the user. In certain embodiments, such a traction device may be used in association with joints other than in the lower spine, such as the neck or knee. In certain embodiments, the traction device is ambulatory, meaning that the traction device is readily portable and wearable during the user's daily activities. The ambulatory nature of the traction device provides more convenience to the user, causes less impact on the user's daily activities, and may lead to quicker healing and recovery than treatment techniques in which the spine is substantially immobilized. Furthermore, the traction device 10 is field adjustable, meaning that the user or another person, such as a field technician associated with a manufacturer of traction device 10, may readily fit traction device 10 to the user at the user's home or other location.

Certain embodiments may provide all, some, or none of these advantages. Certain embodiments may provide one or more other technical advantages, one or more of which may be readily apparent to those skilled in the art from the figures, description and claims included herein.

BRIEF DESCRIPTION OF THE DRAWINGS

To provide a more complete understanding of the present invention and the features and advantages thereof, reference is made to the following description taken in conjunction with the accompanying drawings, in which.

DETAILED DESCRIPTION OF EXAMPLE EMBODIMENTS

Figure 1:
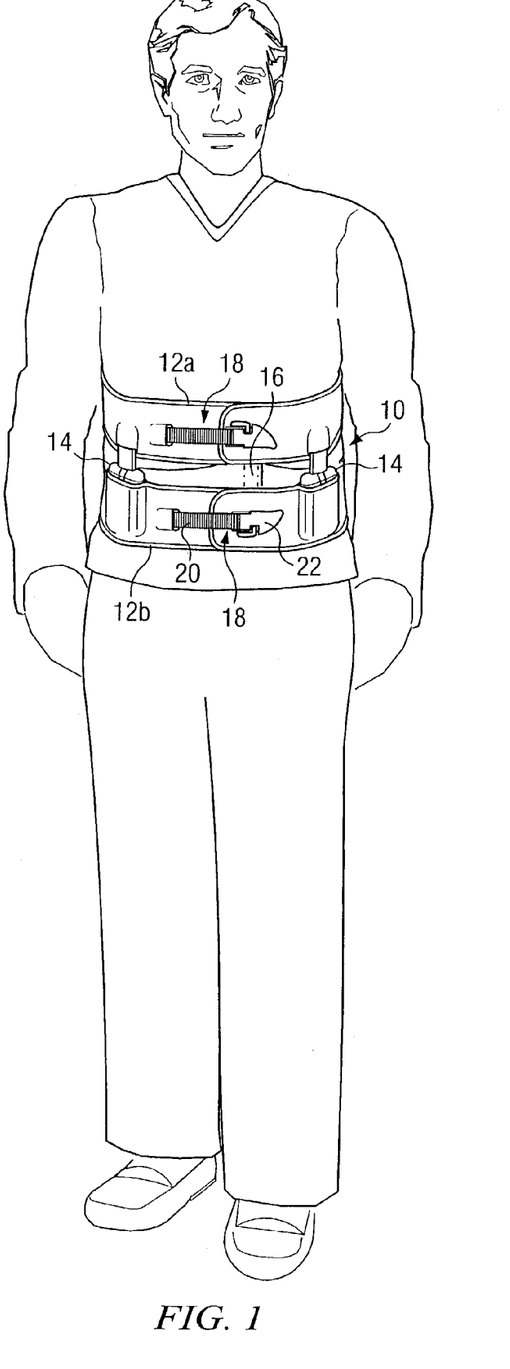
FIG. 1 illustrates a user wearing an example field adjustable traction device.

FIG. 1 illustrates a user wearing an example field adjustable traction device 10. In the illustrated embodiment, traction device 10 applies decompressive forces to the user's spine, which transfers body weight from the user's upper torso to the user's hips to reduce compression and aggravation of low back injuries or other conditions. Traction device 10 may also help stabilize the torso, while still allowing flexibility. This stabilization may help prevent additional compressive forces in the spine due to bending and lifting. In other embodiments, traction device 10 may be modified to apply decompressive forces with respect to other suitable portions of the body, such as the neck or knee for example.

In one embodiment, traction device 10 includes upper and lower support belts 12a and 12b, respectively; however, in other embodiments decompression forces may be generated through various combinations of one or more support belts 12 according to particular needs. Support belts 12 may be formed in any suitable manner that allows them to be positioned around a desired portion of the user's body to transfer decompressive forces to that portion of the user's body. Example support belts 12 are described in greater detail below with reference to FIG. 2.

Traction device 10 also includes one or more lifting mechanisms 14. Lifting mechanisms 14 generate decompressive, or tensile, forces that may be transferred to the user's spine through support belts 12 to "offload" and relieve stress on the spine. In one embodiment, lifting mechanisms 14 are fluidic (for example, pneumatic or hydraulic) devices that generate the desired decompressive forces in response to fluid pressure supplied by a manual pump, an automatic control system, or in any other suitable manner. When pressurized, lifting mechanisms 14 push upward on support belt 12a and downward on support belt 12b, resulting in a decompressive force on the user's spine. However, lifting mechanisms 14 may include other suitable mechanical or electromechanical devices according to particular needs. In one embodiment, two lifting mechanisms 14 are positioned towards the front of the user, one on either side of center, and two lifting mechanisms 14 are positioned towards the rear of the user, one on either side of center.

Although traction device 10 incorporating lifting mechanisms 14 that couple support belts 12 is primarily described, in alternative embodiments the fastening mechanism described below may be incorporated into any suitable support device, whether the support device is designed to provide traction using lifting mechanisms 14 that couple support belts 12, stabilization using rigid, resistive, or other elements that couple support belts 12, or other results. Furthermore, although the fastening mechanism is primarily described as being used in connection with each of two support belts 12, the present invention contemplates use of the fastening mechanism in connection with one, two, or any number of support belts for a wearable support device according to particular needs.

Proper fitting of traction device 10 about the user's body may be important for proper effectiveness. Traction device 10 is field adjustable, meaning that the user or another suitable person, such as a field technician associated with a manufacturer of traction device 10, may readily fit traction device 10 to the user at the user's home or other location. In contrast, previous techniques for fitting a traction device to a user have required a measurement to be taken of one or more portions of the user's body, such as around the user's body under the ribs and above the pelvis where the upper and lower support belts, respectively, would be positioned. Then, the measurements would be communicated to the manufacturer to allow the manufacturer to build a traction device customized for the user. Finally, the traction device would be shipped to the user for use. This process would typically require a number of weeks, which would in turn delay the user's rehabilitation and prolong the length of time that the user was incapacitated. Being field adjustable, traction device 10 overcomes these problems. In one embodiment, as described more fully below with reference to FIG. 2, field adjustability of traction device 10 is provided using fastener inserts and fastener rings that cooperate to secure components of supports belts 12 to one another such that support belts 12 have lengths appropriate for the user. However, in other embodiments, other elements may cooperate to secure components of support belts 12 to one another.

Following use of the fastener inserts and fastener rings, or other suitable components, for macro-adjustment of traction device 10, fitting of traction device 10 to the user may be completed using a pair of common straps 16, each coupled to both upper support belt 12a and lower support belt 12b, and a pair of locking mechanisms 18, one located on upper support belt 12a and one located on lower support belt 12b. In one embodiment, as described more fully below with reference to FIG. 2, each common strap 16 is coupled to both support belts 12 such that common straps 16 allows for uniform simultaneous adjustment of support belts 12. This may be an aspect of the macro-adjustment of traction device 10. Each locking mechanism 18 includes a notched strap 20 and a latch 22 for securing notched strap 20 at a desired notch location. Latch 22 may operate as a detent mechanism with notched strap 20 such that repetitive in and out movement of a handle of latch 22 advances notched strap 20 through latch 22 one notch at a time. This may be an aspect of micro-adjustment of traction device 10. However, locking mechanisms 18 may be replaced with any suitable mechanisms for securing support belts 12 in a desired position, such as snaps, hook and loop fasteners, or any other suitable fasteners.

In operation, the user places traction device 10 around the user's waist and may adjust support belts 12 to a desired tension using common straps 16. Common straps 16 facilitate quick and error-free macro-adjustment of both support belts 12 simultaneously. Common straps 16 similarly facilitate achieving uniform tightness of both support belts 12. The user may then micro-adjust and secure support belts 12 in the desired position using locking mechanisms 18. In one embodiment, to place the user's spine in desired traction, a fluid is supplied to lifting mechanisms 14 to cause lifting mechanisms 14 to expand, pushing upper support belt 12a upward against the user's ribs and lower support belt 12b downward against the user's pelvis. Because support belts 12 are snugly wrapped around the user's body, this decompressive force is transferred to the user's spine, at least some of the user's upper body weight being offloaded from the spine to relieve stress on the spine. Traction device 10 may be portable and wearable during everyday activities. Thus, traction device 10 may be applied and worn at home, at work, at play, during travel, or otherwise at the user's convenience. As a result, the user is more likely to comply with rehabilitative therapy guidelines than if the user was required to travel to a clinic for therapy.

Figure 2:
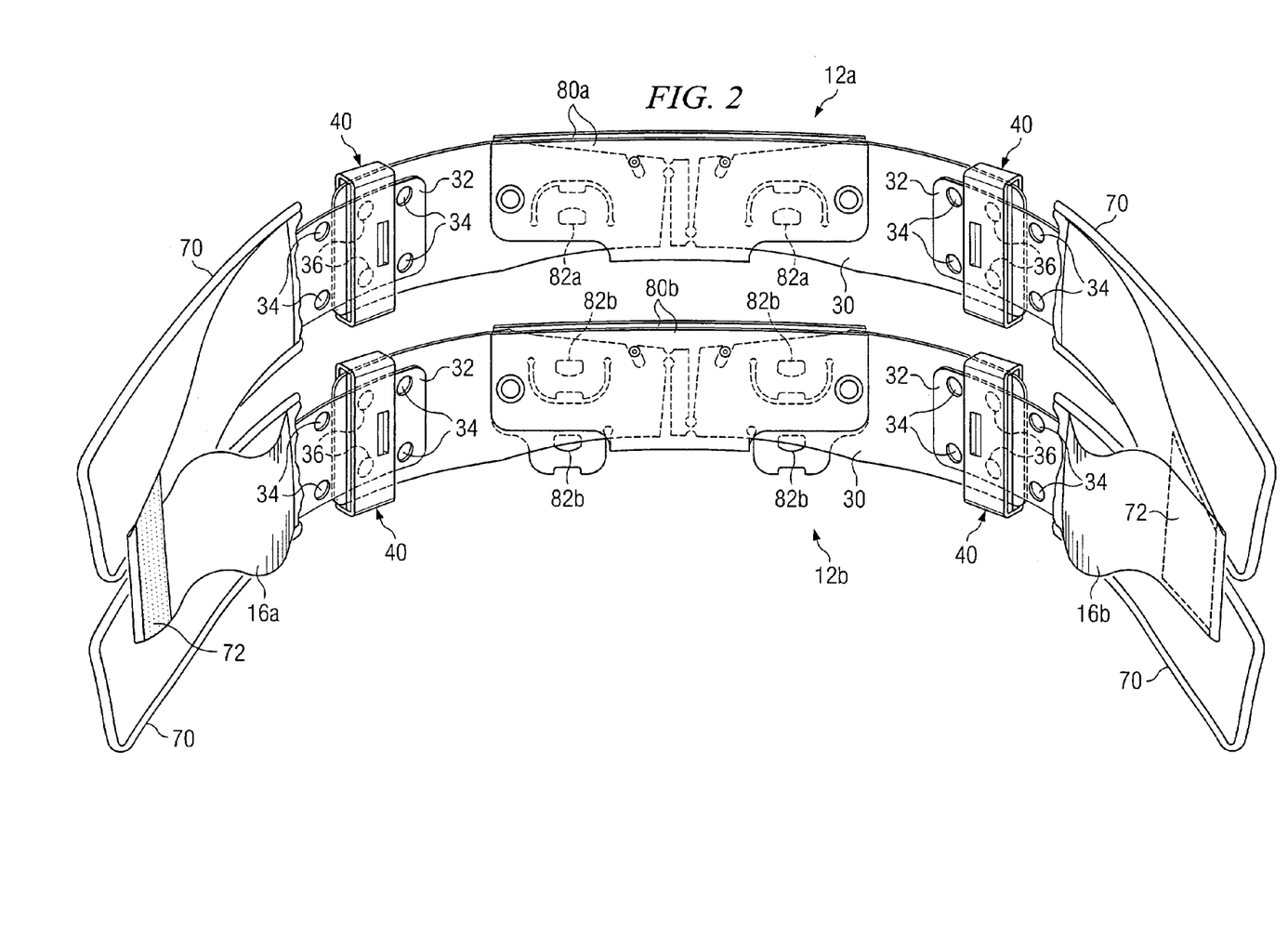
FIG. 2 is illustrates example support belts of a field adjustable traction device.

FIG. 2 illustrates example support belts 12. In one embodiment, each support belt 12 is formed from a back strap 30 and a pair of front straps 32 adjustably fastened to back strap 30 during fitting of traction device 10 for the user. Each front strap 32 is formed with a series of pairs of holes 34 that during fitting may be aligned with a pair of holes 36 formed in the corresponding side of back strap 30. Each front strap 32 is independently fastened to back strap 30 at the pair of holes 36 formed in back strap 30 using a selected one of the series of pairs of holes 34 formed in front strap 32. Each front strap 32 is fastened at a selected pair of holes 34 to back strap 30 using a fastening mechanism 40, which in one embodiment includes a fastener insert and a fastener ring as described below with reference to FIGS. 3A and 3B, respectively. However, in other embodiments, fastening mechanism 40 may include other suitable components. Back strap 30 and front straps 32 are generally rigid in the direction of support (vertically when support belts 12 are placed around the user's body), flexible transverse to the direction of support (horizontally when support belts 12 are placed around the user's body), and may be formed from plastic or any other suitable material.

Figure 3A:
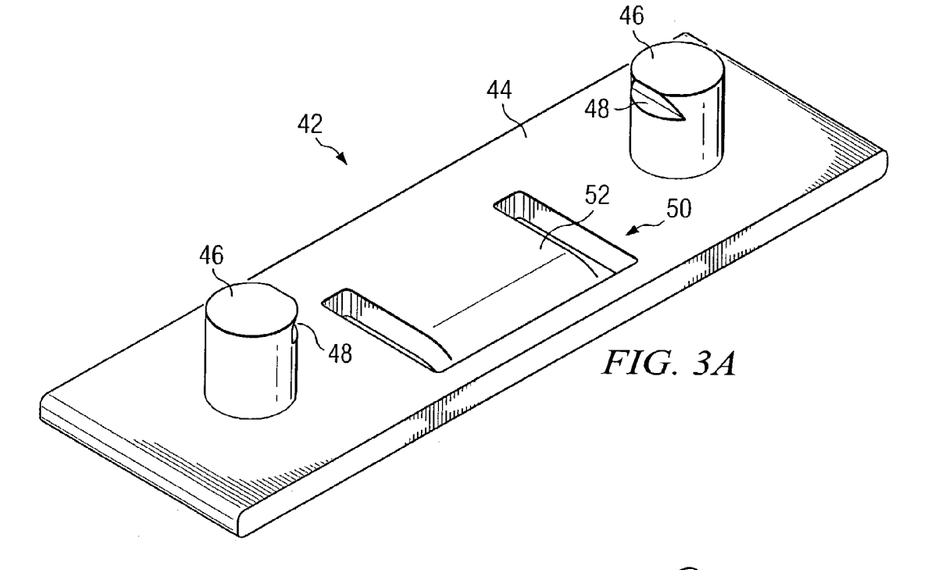
FIGS. 3A and 3B illustrate an example fastener insert and an example fastener ring, respectively, of an example fastening mechanism of a field adjustable traction device.

FIG. 3A illustrates an example fastener insert 42 that includes a base 44 and a pair of posts 46 configured to be inserted through and engage with the pair of holes 36 formed in back strap 30 and also the selected pair of holes 34 formed in front strap 32. Posts 46 may be integrated with base 44 or may be separate components coupled to base 44 in any appropriate manner. The free end of each post 46 includes a notch, slot, or other cut-out 48, such as a triangular dovetail cut-out 48 as shown in FIG. 3A. Cut-outs 48 are configured to mate with and engage corresponding channels in the fastener ring, as described below with reference to FIG. 3B. Base 44 may include a flexible snap-lock mechanism 50 having a tab 52 biased away from the free ends of posts 46 and configured to secure fastener insert 42 to the fastener ring when cut-outs 48 are fully engaged with the corresponding channels of the fastener ring. Fastener insert 42 may be formed from plastic or any other suitable material.

Figure 3B:
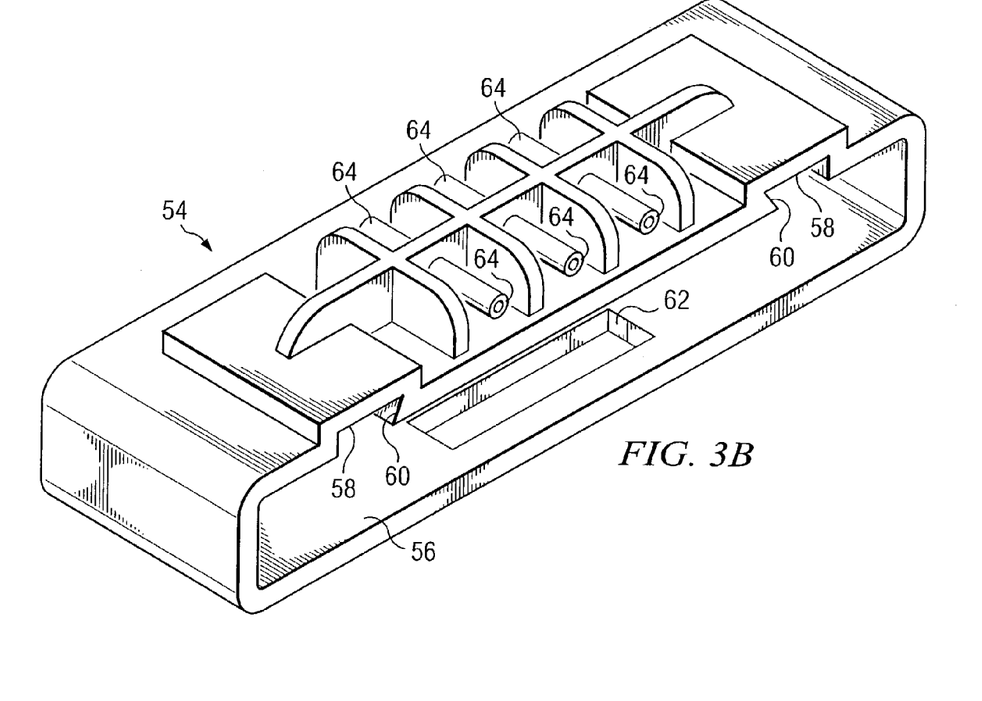

FIG. 3B illustrates an example fastener ring 54 that includes a generally rectangular body 56 configured to surround fastener insert 42, the engaged portion of back strap 30, and the engaged portion of front strap 32. Fastener ring 54 includes a pair of channels 58 each configured to mate with and engage a corresponding post 44 of fastener insert 42. Accordingly, each channel 58 preferably includes a notch, slot, or other cut-out 60, such as a triangular dovetail cut-out 60 as shown in FIG. 3B. Cut-outs 60 are configured to mate with and engage corresponding cut-outs 48 in posts 46. Fastener ring 54 may also include an opening 62 configured to receive and accommodate tab 52 of snap-lock mechanism 50 to secure fastener insert 42 to fastener ring 54 when posts 46 are fully engaged with corresponding channels 58. In an embodiment in which lifting mechanisms 14 are fluidic, fastener ring 54 may also include one or more tube fittings 64 that provide connections for tubes used to supply fluid to lifting mechanisms 14. Use of tube fittings 64 may allow tubes associated with front strap 32 to be cut to length during fitting of traction device 10 for the user, the free ends of the tubes being pushed over the free ends of tube fittings 64 once front strap 32 is fastened to back strap 30 using fastening mechanism 40. Fastener ring 54 may be formed from plastic or any other suitable material.

Although a series of pairs of holes 34, a pair of holes 36, a pair of posts 46, and a pair of channels 58 are described, the present invention contemplates a series of single holes 34, one hole 36, one post 46, and one channel 58. Similarly, the present invention contemplates a series of three holes 34, three holes 36, three posts 46, and three channels 58. Any suitable numbers of these elements may be used according to particular needs. In one embodiment, pairs are used to prevent rotation of front strap 32 relative to back strap 30.

Figure 4A:
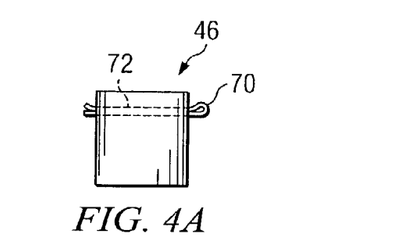
FIGS. 4A through 4C illustrate example alternatives to a fastener ring.
Figure 4B:
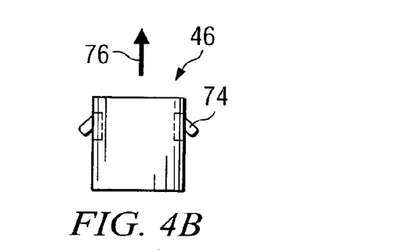
Figure 4C:
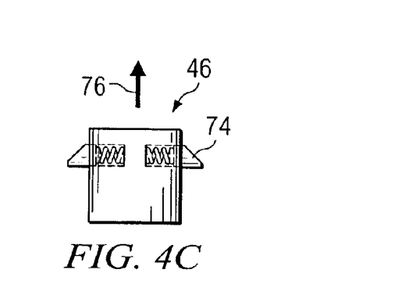

Although fastening mechanism 40 is primarily described as including fastener insert 42 and fastener ring 54, fastening mechanism 40 may include any components suitable to secure front strap 32 in position relative to back strap 30 using holes 34 and holes 36, respectively. For example, as illustrated in FIG. 4A, in an alternative embodiment fastening ring 54 may be replaced with one or more pins 70 each adapted to be removably inserted through a channel 72 in the exposed end of a post 46 of fastener insert 42 such that pin 70 extends from the sides of post 46 and prevents post 46 from retracting through holes 34 and 36, thereby securing fastener insert 42 in place and thus securing front strap 32 in position relative to back strap 30. As other examples, as illustrated in FIGS. 4B and 4C, in other alternative embodiments fastening ring 54 may be eliminated and one or more posts 46 of fastener insert 42 may each be configured with retractable wings, flaps, or other suitable structures 74 that retract into post 46 in response to pressure but remain extended to the sides of post 46 absent such pressure. Structures 74 may be angled away from the exposed end of post 46, toward base 44 of fastener insert 42, to facilitate retraction into post 46 in response to pressure in the direction of arrows 76. As the exposed end of post 46 is inserted through holes 36 and 34, structures 74 contact back strap 30 and front strap 32 surrounding holes 36 and 34, respectively, and retract into post 46. Once structures 74 clear hole 34 of front strap 32, structures 74 extend from the sides of post 46 and prevent post 46 from retracting through holes 34 and 36, thereby securing fastener insert 42 in place and thus securing front strap 32 in position relative to back strap 30. In these or other alternative embodiments, where fastener ring 54 is replaced or eliminated, snap-lock mechanism 50 may similarly be eliminated from fastener insert 42. Furthermore, in these or other alternative embodiments, the one or more posts 46 may all extend from fastener insert 42 as illustrated in FIG. 3A, may all extend from another single base or other suitable structure, or may each extend from an independent base or other suitable structure according to particular needs.

Referring again to FIG. 2 and also to FIGS. 5A through 5E, to fit traction device 10 to the user using fastening mechanisms 40, a field technician or another suitable person takes one or more measurements, such as around the user's body under the ribs and above the pelvis where upper support belt 12a and lower support belt 12b, respectively, would be positioned during use. Front straps 32 are preferably manufactured to be long enough for the largest anticipated user, such that the person fitting traction device 10 to the user may cut front straps 32 individually to length based on the user's measurements. Once a front strap 32 has been cut to length, in one embodiment, a fastener ring 54 may be placed over the appropriate end of back strap 30 (FIG. 5A) or, alternatively, over the cut end of front strap 32. Fastener ring 54 is preferably oriented such that tube fittings 64 will be positioned on the outside, the side farthest from the user when support belt 12 is positioned on the user's body.

Figure 5A:
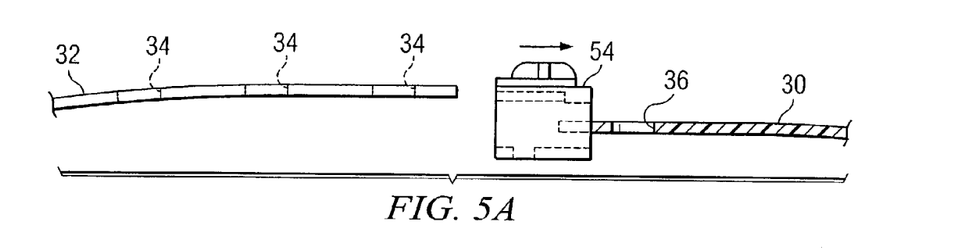
FIGS. 5A through 5E illustrate using an example fastening mechanism to fit a field adjustable traction device to a user.
Figure 5B:
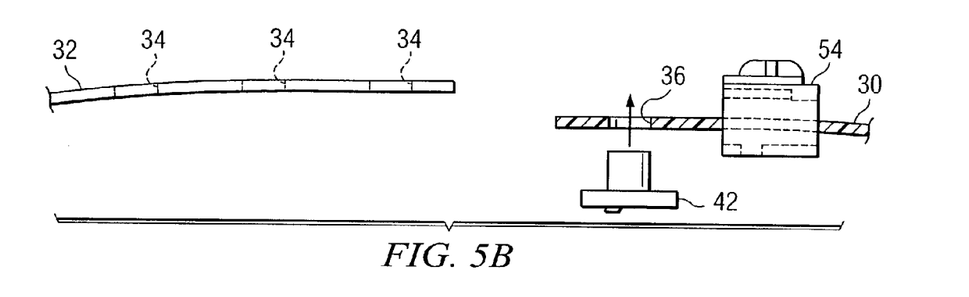
Figure 5C:
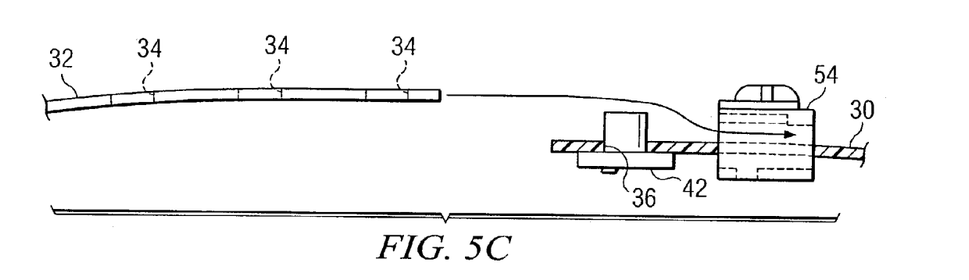
Figure 5D:
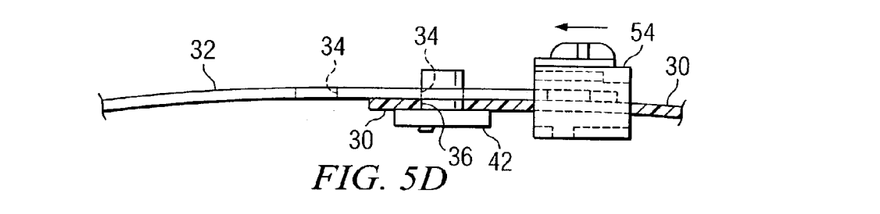
Figure 5E:
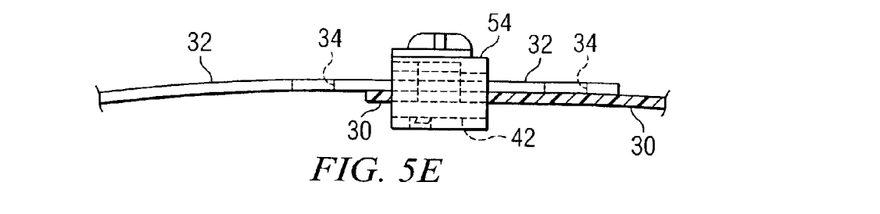

Next, in one embodiment, fastener insert 42 is inserted from the inside, the side nearest the user when support belt 12 is positioned on the user's body, through the pair of holes 36 formed in back strap 30 such that posts 46 are on the same side of support belt 12 as channels 58 of fastener ring 54 and the free end of tab 52 of snap-lock mechanism 50 is pointed away from fastener ring 54 (FIG. 5B). The selected pair of holes 34 formed in front strap 32 are placed over posts 46 protruding through back strap 30 (FIG. 5C). Fastener ring 54 is then guided towards posts 46 (FIG. 5D), surrounding both back strap 30 and front strap 32, and cut-outs 48 of posts 46 are guided into mating engagement with cut-outs 60 of channels 58. Fastener ring 54 is moved over posts 46 until tab 52 of snap-lock mechanism 50 drops into place in opening 62 to secure front strap 32 relative to back strap 30 (FIG. 5E). Finally, in an embodiment in which lifting mechanisms 14 are fluidic, the tubes used to supply fluid to lifting mechanisms 14 associated with front strap 32 are pushed over the free ends of tube fittings 64.

In one embodiment, an outer sleeve 70 substantially encases each support belt 12. Portions of outer sleeve 70 are cut away in FIG. 2 for clarity. Outer sleeve 70 preferably provides an attractive look to support belt 12 and also may provide cushioning comfort to the user. Outer sleeve 70 may be formed from fabric or other suitable material and may be formed in multiple sections to facilitate selective access to back strap 30 and front straps 32 for adjustment, for example, selective access to fastening mechanisms 40. Also shown more clearly in FIG. 2 is common strap 16 incorporating opposing common strap portions 16a and 16b. As described above, common strap 16 connects to both support belts 12, allowing common simultaneous macro-adjustment of support belts 12 about the user's body. In one embodiment, hook and loop fasteners 72 are disposed on opposing common strap portions 16a, 16b to secure common strap 16 about the user's body.

In one embodiment, the back strap 30 of each support belt 12 is sandwiched between two back panels 80, one being positioned to the outside of support belt 12 to accommodate any lifting mechanisms 14 and the other being positioned to the inside of support belt 12 to provide additional rigidity. As described more fully below with reference to FIGS. 6A and 6B, back panels 80 may be coupled to back strap 30 and to one another such that opposing portions of back strap 30 are allowed to rotate relative to back panels 80 to conform support belt 12 to the underlying bone structure and natural generally conical shapes of the user's body. Back panels 80 may be disposed at least in part within outer sleeves 70 of support belts 12. Back panels 80 are generally rigid in the direction of support (vertically when support belts 12 are placed around the user's body) and like support belts 12 may be formed from plastic or any other suitable material. Back panels 80 may each include openings 82 to receive clips of lifting mechanisms 14 positioned towards the rear of the user, facilitating the transfer of decompressive forces from lifting mechanisms 14 to support belts 12 when lifting mechanisms 14 force upper support belt 12a and lower support belt 12b in opposite directions.

Figure 6A:
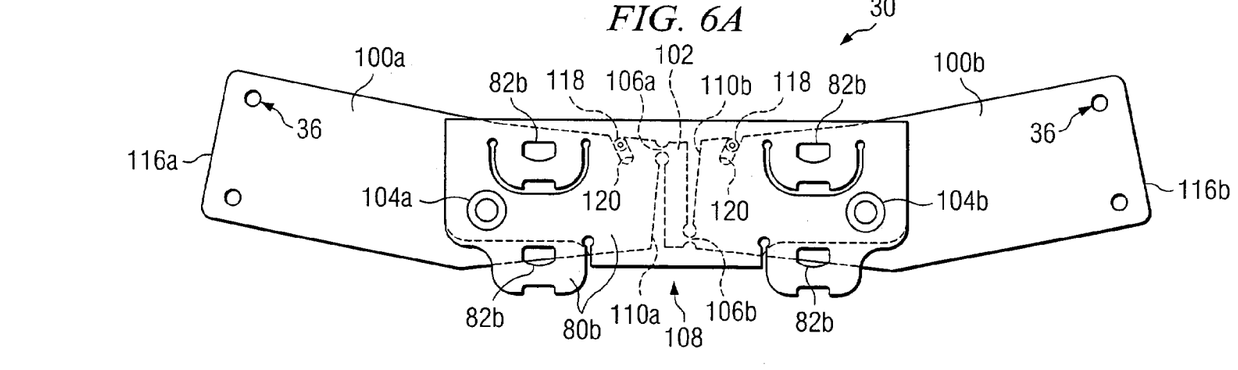
FIGS. 6A and 6B illustrate an example back strap of a field adjustable traction device with an associated example canting mechanism.

FIG. 6A illustrates an example back strap 30 of lower support belt 12b, viewed from the rear. Although back strap 30 and back panel 80b of lower support belt 12b are described, an analogous description may apply to back strap 30 and back panel 80a of upper support belt 12a. Furthermore, although back strap 30 and front straps 32 are described, in an alternative embodiment support belt 12 may include a single belt that operates similarly to support belt 12 including back strap 30 and front straps 32 with respect to the features described below.

In one embodiment, back strap 30 includes opposing side portions 100a and 100b coupled to one another using a central portion 102. Each side portion 100 is rotatably coupled between back panels 80 at a corresponding pivot 104 using a rivet or other component. Any suitable component may be used to couple back strap 30 between back panels 80 at pivots 104 so as to allow side portions 100 to rotate relative to back panels 80. In a particular embodiment, side portion 100a is coupled to central portion 102 using a hinge 106a located near the top (or bottom) of back strap 30 and side portion 100b is coupled to central portion 102 using a hinge 106b located near the bottom (or top) of back strap 30. Rotational movement of side portion 100a with respect to pivot 104a (e.g., vertically down) will thus be transferred through hinges 106a and 106b to cause rotational movement of side portion 100b with respect to pivot 104b in the same direction (e.g., vertically down) and in substantially the same amount. Central portion 102 and hinges 106a, 106b collectively form a canting mechanism 108 linking opposing side portions 100 of back strap 30. When support belt 12 is positioned around the user's body, canting mechanism 108 allows side portions 100 of back strap 30, which may be coupled to front straps 32, to maintain substantial symmetry and conform to the contours of the user's body, particularly to the underlying bone structure and natural generally conical shapes of the user's torso under the ribs (upper support belt 12) and above the pelvis (lower support belt 12). Therefore, canting mechanism 108 may allow traction device 10 to be properly and comfortably fit to users having a wide variety of sizes and shapes.

Figure 6B:
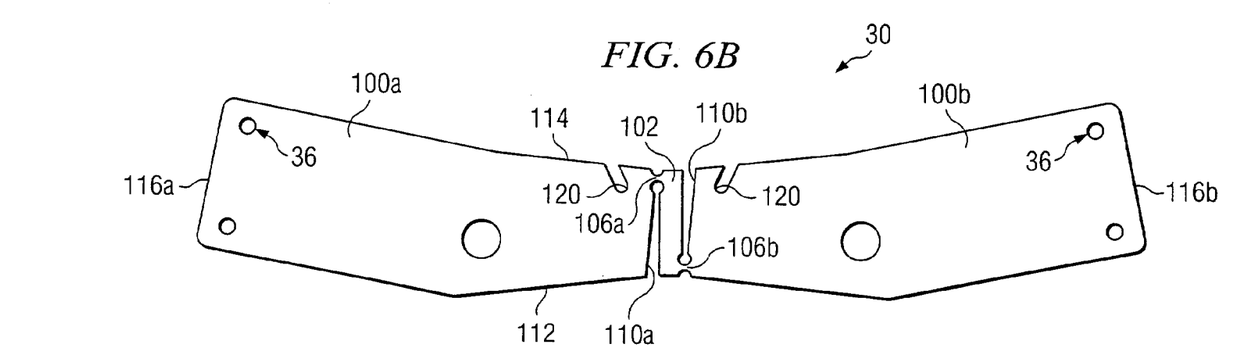

FIG. 6B illustrates example back strap 30 without back panels 80 for more clarity. As illustrated more clearly in FIG. 6B, side portions 100 and canting mechanism 108 may be integrally formed, for example, from a single piece of plastic. Hinges 106 may be formed by molding or cutting this single piece of plastic into the desired shape; however, any other suitable method of fabricating these components may be used. In one embodiment, hinges 106a, 106b may be formed by molding or cutting slots 110a, 110b in back strap 30. The term "slots" is meant to include slits, wedges, or the like formed in back strap 30. If slots 110 are formed as slits 110, then slits 110 may be pulled open to create wedges when back strap 30 is coupled between back panels 80.

As shown in FIG. 6B, slot 110a associated with hinge 106a begins at a first (bottom or top) edge 112 of back strap 30 and extends almost to a second (top or bottom) edge 114 of back strap 30. The remaining material between the end of slot 110a and second edge 114 of back strap 30 forms hinge 106a. A circular or other cut-out may be formed at the end of slot 110a, adjacent hinge 106a, to assist in opening slot 214 and to reduce the resultant stresses on hinge 106a. Slot 110b may be formed in a similar manner except that slot 110b begins at second edge 114 of back strap 30 and extends almost to first edge 112. Hinge 106b is located proximate to first edge 112 and provides a different point of rotation than hinge 106a proximate second edge 114. Therefore, hinges 106a, 106b may be referred to collectively referred to as a polycentric hinge.

If slots 110 are formed as wedges 110 in back strap 30, the width of wedges 110 and the angle at which wedges 110 are formed determines, at least in part, the range of movement of side portions 100. For example, the greater the size of wedges 110, the more range of movement that side portions 100 will be permitted. If slots 100 are formed as slits 110, then as described above slits 110 may be opened to form wedges 110 having an appropriate size. Furthermore, the positioning of hinges 106 ensures that the movement of side portions 100 are complementary. For example, as described above, referring to FIG. 6A, if an end 116a of side portion 100a moves up, then an opposing end 116b of opposing side portion 100b will also move up in a substantially equal amount. This is because the upward movement of end 116a will cause slot 110a to close about hinge 106a, this closure of hinge 106a will in turn cause slot 110b to close about hinge 106b due to the forces applied and the positioning of pivots 104, and this closure of hinge 106b will in turn cause an upward movement of end 116b. Therefore, in one embodiment, the design of canting mechanism 108 synchronizes the movements of side portions 100 and requires movement of side portions 100 to be in the same direction and in a substantially equal amount.

Referring again to FIG. 6A, depending upon which part of the user's body support belt 12 is to be positioned around, one or more limiters 118 and associated limiter slots 120 formed in back strap 30 may be used to limit the movement of side portions 100 in one or more directions. For example, if lower support belt 12b is to be positioned around the user's torso above the pelvis and limiters 118 are engaged with associated limiter slots 120, limiters 118 may allow side portions 100 to move upward to accommodate the user's hips while preventing downward movement of side portions 100 past a certain point. In one embodiments, limiters 118 are peg-like extensions that are coupled to or integrated with a back panel 80 and extend into the region between back panels 80. Although limiting the downward movement of side portions 100 of lower support belt 12b is described in detail, analogous limiters 118 and associated limiter slots 120 may be provided to limit the upward movement of side portions 100 of upper support belt 12a.

Although the present invention has been described with several embodiments, a plethora of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A field adjustable traction device, comprising:
   a first support belt;
   a second support belt separated from the first support belt such that a user's joint may be positioned between the support belts; and
   one or more lifting mechanisms coupling the support belts and operable to apply a decompressive force to the joint through the support belts;
   each support belt comprising:
      a back strap comprising first and second ends, a set of one or more holes being formed in the back strap proximate the first end and a set of one or more holes being formed in the back strap proximate the second end;
      first and second front straps adjustably fastened to the first and second ends of the back strap, respectively, a plurality of sets of one or more holes being formed in the first front strap, each set of one or more holes formed in the first front strap being configured to selectively align with the set of one or more holes proximate the first end of the back strap, a plurality of sets of one or more holes also being formed in the second front strap, each set of one or more holes formed in the second front strap being configured to selectively align with the set of one or more holes proximate the second end of the back strap;
      for each front strap, a set of one or more posts operable to be inserted through the set of one or more holes formed in the back strap proximate a corresponding end of the back strap and also through a selected one of the sets of one or more holes formed in the front strap to position the front strap relative to the back strap; and
      for each front strap, a mechanism operable to engage the set of one or more posts to secure the front strap in position relative to the back strap;
   wherein for each front strap:
   the set of one or more posts extend from a base of an insert; and
   the mechanism comprises a ring comprising a body and a set of one or more channels formed in the body, the set of one or more channels of the ring operable to engage with the set of one or more posts of the insert to secure the front strap in position relative to the back strap when the ring is positioned around the back strap, front strap, and insert proximate the selected set of one or more holes formed in the front strap.

2. The device of claim 1, wherein each post of the insert comprises a notch configured to slidingly engage with a notch of a corresponding channel of the ring, the engaged posts and notches preventing retraction of the insert from the set of one or more holes formed in the back strap proximate the corresponding end of the back strap and from the selected set of one or more holes formed in the front strap.

3. The device of claim 1, wherein:
   the ring comprises an opening formed in the body;
   the insert comprises a snap-lock mechanism formed in the base, the snap-lock mechanism comprising a tab biased away from the posts and operable to drop into the opening formed in the ring when the posts are fully engaged with the channels to secure the ring in position.

4. A method of fitting a field adjustable traction device to a user, the traction device having a first support belt, a second support belt separated from the first support belt such that a joint of the user may be positioned between the support belts, and one or more lifting mechanisms coupling the support belts and operable to apply a decompressive force to the joint through the support belts, each support belt comprising a back strap and two front straps each coupled to a corresponding end of the back strap, the method comprising:

aligning a selected one of a plurality of sets of one or more holes formed in a front strap of a support with a set of one or more holes formed in a back strap of the support proximate an end of the back strap;

inserting a set of one or more posts through the set of one or more holes formed in the back strap and also through the selected set of one or more holes formed in the front strap to position the front strap relative to the back strap;

engaging the set of one or more posts to secure the front strap in position relative to the back strap;

wherein:

the set of one or more posts extend from a base of an insert; and     the set of one or more posts are engaged using a ring comprising a body and a set of one or more channels formed in the body, the set of one or more channels of the ring operable to engage with the set of one or more posts of the insert to secure the front strap in position relative to the back strap when the ring is positioned around the back strap, front strap, and insert proximate the selected set of one or more holes formed in the front strap.

5. The method of claim 4, wherein each post of the insert comprises a notch configured to slidingly engage with a notch of a corresponding channel of the ring, the engaged posts and notches preventing retraction of the insert from the set of one or more holes formed in the back strap proximate the end of the back strap and from the selected set of one or more holes formed in the front strap.

6. The method of claim 4, wherein:

the ring comprises an opening formed in the body;

the insert comprises a snap-lock mechanism formed in the base, the snap-lock mechanism comprising a tab biased away from the posts and operable to drop into the opening formed in the ring when the posts are fully engaged with the channels to secure the ring in position.

7. The method of claim 4, further comprising:

placing the ring over the end of the back strap;

before the aligning and inserting steps, guiding the ring along the back strap away from the end of the back strap to expose the end of the back strap; and     after the aligning and inserting steps, guiding the ring along the back strap towards the end of the back strap such that the set of one or more posts of the insert engages with the set of one or more channels of the ring.

8. The method of claim 4, further comprising guiding the ring along the back strap towards the end of the back strap until:

the set of one or more posts of the insert are fully engaged with the set of one or more channels of the ring; and     a tab formed in the base of the insert and biased away from the posts drops into an opening formed in the ring to secure the ring in position.

9. The method of claim 4, wherein the traction device comprises an ambulatory spinal traction device and the joint comprises at least a portion of the user's spine.

10. The method of claim 4, wherein the lifting mechanisms comprise fluidic lifting mechanisms operable to apply the decompressive force in response to an increase in fluid pressure within the lifting mechanisms.

11. The method of claim 4, wherein the back strap and front straps for each support are formed from plastic and are generally rigid in a direction in which the decompressive force is applied.

12. The method of claim 4, wherein:

the set of one or more holes formed proximate the end of the back strap comprises two vertically aligned holes, one formed proximate a top edge of the back strap and one formed proximate a bottom edge of the back strap; and     each set of one or more holes formed in the front strap comprises two vertically aligned holes, one formed proximate a top edge of the front strap and one formed proximate a bottom edge of the front strap.

* * * * *